US012779071B2

(12) United States Patent
Raikhlin (Yaloz) et al.

(10) Patent No.: US 12,779,071 B2
(45) Date of Patent: Nov. 3, 2026

(54) ENVIRONMENTALLY FRIENDLY OZONE DISINFECTANT DEVICE

(71) Applicant: ORAVEL LTD., Beer Yaakov (IL)

(72) Inventors: Ortal Raikhlin (Yaloz), Nesher (IL); Eliahu Maier, Tel Aviv (IL); Avraham Peretz, Beer Yaakov (IL)

(73) Assignee: ORAVEL LTD., Beer Yaakov (IL)

( * ) Notice: Subject to any disclaimer, the term of this patent is extended or adjusted under 35 U.S.C. 154(b) by 593 days.

(21) Appl. No.: 18/265,347

(22) PCT Filed: Dec. 7, 2021

(86) PCT No.: PCT/IL2021/051458
§ 371 (c)(1),
(2) Date: Jun. 5, 2023

(87) PCT Pub. No.: WO2022/123562
PCT Pub. Date: Jun. 16, 2022

(65) Prior Publication Data
US 2024/0050610 A1 Feb. 15, 2024

Related U.S. Application Data

(60) Provisional application No. 63/122,578, filed on Dec. 8, 2020.

(51) Int. Cl.
*A61L 2/20* (2026.01)
*A61L 2/202* (2026.01)

(52) U.S. Cl.
CPC ......... *A61L 2/202* (2013.01); *A61L 2202/122* (2013.01); *A61L 2202/14* (2013.01)

(58) Field of Classification Search
CPC . A61L 2/202; A61L 2202/122; A61L 2202/14
See application file for complete search history.

(56) References Cited

U.S. PATENT DOCUMENTS 5,725,762 A * 3/1998 Beal ........................ B01D 21/02 210/512.1
5,853,579 A * 12/1998 Rummler ............... B01D 46/42 110/235
(Continued)

FOREIGN PATENT DOCUMENTS

CN 102062430 A * 5/2011
CN 106798596 A * 6/2017
(Continued)

OTHER PUBLICATIONS

Chun-Chieh Tseng et al. "Ozone for Inactivation of Aerosolized Bacteriophages"; Aerosol science and Technology, 2006, 40, (9) 683-689. DOI: 10.1080/02786820600796590.

*Primary Examiner* — Regina M Yoo
(74) *Attorney, Agent, or Firm* — The Roy Gross Law Firm, LLC; Roy D. Gross

(57) ABSTRACT

Disinfection device against viruses, bacteria and other microorganisms using ozone without contaminating the environment with ozone or users cross contamination. Disinfection is obtained by inserting an organ (e.g. hands) into a chamber containing a predetermined ozone concentration for a predetermined time. A suction duct surrounds the chamber. Ambient air mixed with overflow ozone from the chamber is fed through the suction duct into an ozone filter, then to an air outlet so the discharged air meets FDA regulation. The top of the chamber can be permanently open for inserting hands without ozone being discharged to the environment.

7 Claims, 8 Drawing Sheets

(56) References Cited

U.S. PATENT DOCUMENTS

| | | | | |
|---|---|---|---|---|
| 6,254,625 | B1 | 7/2001 | Rosenthal et al. | |
| 6,391,259 | B1 | 5/2002 | Malkin et al. | |
| 10,258,704 | B2 * | 4/2019 | Blakeman | A61L 2/202 |
| 11,000,611 | B1 * | 5/2021 | He | A61L 2/202 |
| 2010/0266446 | A1 | 10/2010 | Constantacos | |
| 2011/0277342 | A1 * | 11/2011 | Ishii | A47K 10/48<br>34/526 |
| 2022/0016287 | A1 * | 1/2022 | He | A61L 2/202 |
| 2023/0211030 | A1 * | 7/2023 | Lloyd | A61L 2/10<br>422/28 |

FOREIGN PATENT DOCUMENTS

| | | | | | |
|---|---|---|---|---|---|
| CN | 107124872 | A | | 9/2017 | |
| CN | 206745647 | U | * | 12/2017 | |
| CN | 212037340 | U | | 12/2020 | |
| DE | 102020112847 | A1 | * | 11/2021 | B05B 7/0012 |
| EP | 0281870 | A2 | | 9/1988 | |
| JP | 3061983 | U | | 9/1999 | |
| JP | 2005177415 | A | * | 7/2005 | |
| JP | 2011104377 | A | | 6/2011 | |
| KR | 100737210 | B1 | | 7/2007 | |
| KR | 100873412 | B1 | | 12/2008 | |
| KR | 20110002182 | U | | 3/2011 | |
| KR | 20110002545 | U | | 3/2011 | |
| KR | 101182835 | B1 | * | 9/2012 | A61L 2/06 |
| WO | WO-9926668 | A1 | * | 6/1999 | A61L 2/10 |
| WO | 00/06209 | A2 | | 2/2000 | |
| WO | WO-2021228682 | A1 | * | 11/2021 | B05B 7/267 |
| WO | WO-2021236816 | A1 | * | 11/2021 | A61L 2/22 |

* cited by examiner

ENVIRONMENTALLY FRIENDLY OZONE DISINFECTANT DEVICE

CROSS REFERENCE TO RELATED APPLICATIONS

This application is a National Phase of PCT Patent Application No. PCT/IL2021/051458 having International filing date of Dec. 7, 2021, which claims the benefit of priority of U.S. Provisional Patent Application No. 63/122,578, filed December 8, 202, the contents of which are all incorporated herein by reference in their entirety.

FIELD OF THE INVENTION

The invention pertains to the field of disinfection devices, in particular ozone disinfection devices.

BACKGROUND OF THE INVENTION

Humanity has experienced in recent years mass pandemics such as Zika, Ebola, and COVID-19. It is predicted that the future holds more plagues to occur.

Studies have found that some pathogens (viruses, fungi and bacteria) spread from person to person mainly through respiratory droplets produced when infected person coughs, sneezes, or talks. Other pathogens can infect a person by touching a surface or object that has the pathogen on it and then touching their own mouth, nose, or eyes.

Disinfection of hands has proven to be an effective tool for reducing the risk of being infected. During the first waves of the COVID-19 pandemic, frequent-hands washing was one of the three most important measures along social distancing and wearing masks which were recommended by the World Health Organization for controlling the pandemic. While this was proven later on to be a lesser rout of spread of the virus, the constant formation of new mutants might produce a new strain that will be infectious through surfaces. There is therefore an acute and urgent need to find a simple and quick mass disinfection method for hands to be used in the entrances and exits of public places such as schools, hospitals, airports, theaters, supermarkets, etc. See for example documents on hand disinfection: *CDC* 2020—*"Hands washing: Clean Hands Save Lives"* (https://www.cdc.gov/handwashing/index.html) and a 2020 MIT study: "*To slow an epidemic, focus on hand washing*" (https://news.mit.edu/2020/slow-epidemic-airport-hand-washing-0206).

Existing disinfection methods, namely soap and water wash, hand sanitizers and UV radiation are not environmental friendly and not suitable for mass disinfection. Soap is not suitable for mass disinfection—it requires installation of running water infrastructure which is not feasible in any location, requires servicing for loading disinfectants, not environmentally friendly and it requires compliance of the public to adequately wash their hands which is not always the case and for which there is no control.

Hand sanitizer is also not suitable for mass disinfection. It requires servicing for loading disinfectants, Classified as Class I Flammable Liquid, leaves chemical leftovers after the alcohol and water evaporate which may be irritant, not environmentally friendly and there is no control over the quality of the disinfection process performed by each individual.

UV disinfection is not suitable for mass disinfection because it does not disinfect places that are shaded from the UV light. In addition, the UV radiation required for microbiological inactivation is harmful for humans, as it poses risk of skin cancer and skin aging.

There is experimental evidence that ozone can be effective for skin disinfection from bacteria, viruses and other microorganisms including SARS-CoV-2, the pathogen of COVID-19, within 15 seconds and with the correct concentration (which is safe for the human skin). See for example Chun-Chieh Tseng et al. *Aerosol science and Technology,* 2006, 40, (9) 683-689.

Ozone can be harmful if it enters the human airways in high concentration. The FDA has set a maximum permitted emission from medical devices of 0.05 PPMV and the OSHA requirement for workers exposure for a long period to ozone is 0.1 PPMV.

The challenge for using ozone, the ultimate disinfection gas for vast reliable and fast hands disinfection from bacteria, viruses and other microorganisms is to avoid depletion and accumulation of Ozone exceeding the FDA and OSHA limits. The described device in this invention meets the above challenge.

SUMMARY OF THE INVENTION

The object of the invention is to provide a mass disinfection device against viruses, bacteria and other microorganisms.

Further objects of the invention are to provide a disinfecting device which is

- effectively and reliably disinfecting
- safe for use
- environmentally friendly and operates according to FDA and OSHA regulations
- free of cross contamination between users
- a low maintenance device
- designed for mass disinfecting, provides feedback if disinfection has been performed properly The hands are vertically inserted into a chamber containing a predetermined ozone concentration for a predetermined time during which the hands are disinfected.

The upper area of the chamber is permanently open to the environment, a continuous flow of ambient air is sucked into the device and sweeps with it a small amount of Ozone that strives to leave the chamber, the mixed flow of ambient air and ozone is sucked into ducts located around the chamber and flows toward the outlet and from their out to the environment or to a central evacuation system. The device may have a catalytic ozone filter that converts the ozone back into oxygen, the ozone concentration that exists the filter meets the FDA standards for medical devices. In such embodiments, the catalytic ozone filter is in fluid communication with the suction duct and the air outlet and disposed upstream the outlet.

The filtered air outlet is sucked by a blower and discharges back to the environment.

The small amount of ozone that the device emits into the environment is decreased dramatically over time due to the short half-life of ozone in fresh ambient air, resulting in quick decomposition back to oxygen.

Ozone is supplied to the chamber by a corona discharged generator which converts the Oxygen in the air to ozone.

The disinfection is done to body organs like hands or to accessories such as masks, gloves, clothing, PPE, etc.

A major advantage of the device in this invention is its flow method in which a small amount of ozone leaves the disinfection chamber and as a result the small ozone filter that is required to discharge air back to the surrounding with a low ozone concentration and according to the FDA standards.

For example-if the bottom of the disinfection chamber is completely open and all the ambient air flows all the way through the disinfection chamber, an unreasonably large ozone filter is required.

In the first aspect the invention provides a disinfection device that includes housing with an opening, an entrance guide wall, a disinfection chamber, a suction duct, an ozone filter in fluid communication with the suction duct and the air outlet, an ozone generator which supplies ozone to the disinfection chamber, a blower and an air outlet.

The opening is located in the upper portion of the housing to allow insertion of an organ to be disinfected. The entrance guide wall is attached to the circumference of the opening.

The disinfection chamber is located below the entrance guide wall and includes a top opening and an ozone distributor being in fluid communication with the ozone generator. The suction duct has an entry which is located between the entrance guide wall and the disinfection chamber and it extends toward the ozone filter. The ozone filter receives a mixture of ambient air and excessive ozone overflow from the disinfection chamber and reduces the amount of ozone in an output air flow. The blower motivates ambient air from the housing opening and excessive ozone overflow from the disinfection chamber through the suction duct, through the ozone filter and discharge airflow from the device through the air outlet to the environment.

In a second aspect, the invention provides a system which includes at least one disinfection device described above except that at least one of the blower, the ozone generator and the ozone filter components are placed outside of the housing, possibly remotely from the device.

Advantages of the Invention

Uses gaseous ozone for disinfection without contaminating the environment with ozone, and according to the FDA regulation for medical devices.

- Operates without risk of cross contamination between different users due to the fact that the chamber is continuously kept under disinfecting high level of Ozone.
- The hands are inserted for a short period into a chamber containing gaseous ozone that is in contact with hands skin and penetrates even under the nails.
- Operates without medical damage to user's skin and no harm to the environment.
- Operates without need for infrastructure or service for loading disinfectants, Ozone gas is generated from ambient air by an ozone generator
- Is suitable for mass disinfection-control of the process ensures that the disinfection is completed and performed correctly.
- The device can be integrated with other devices or accessories, for example, a door that opens only if disinfection has been performed correctly, or a temperature measuring sensor that measures the hands temperature, etc.

DETAILED DESCRIPTION OF THE INVENTION

Figure 1:
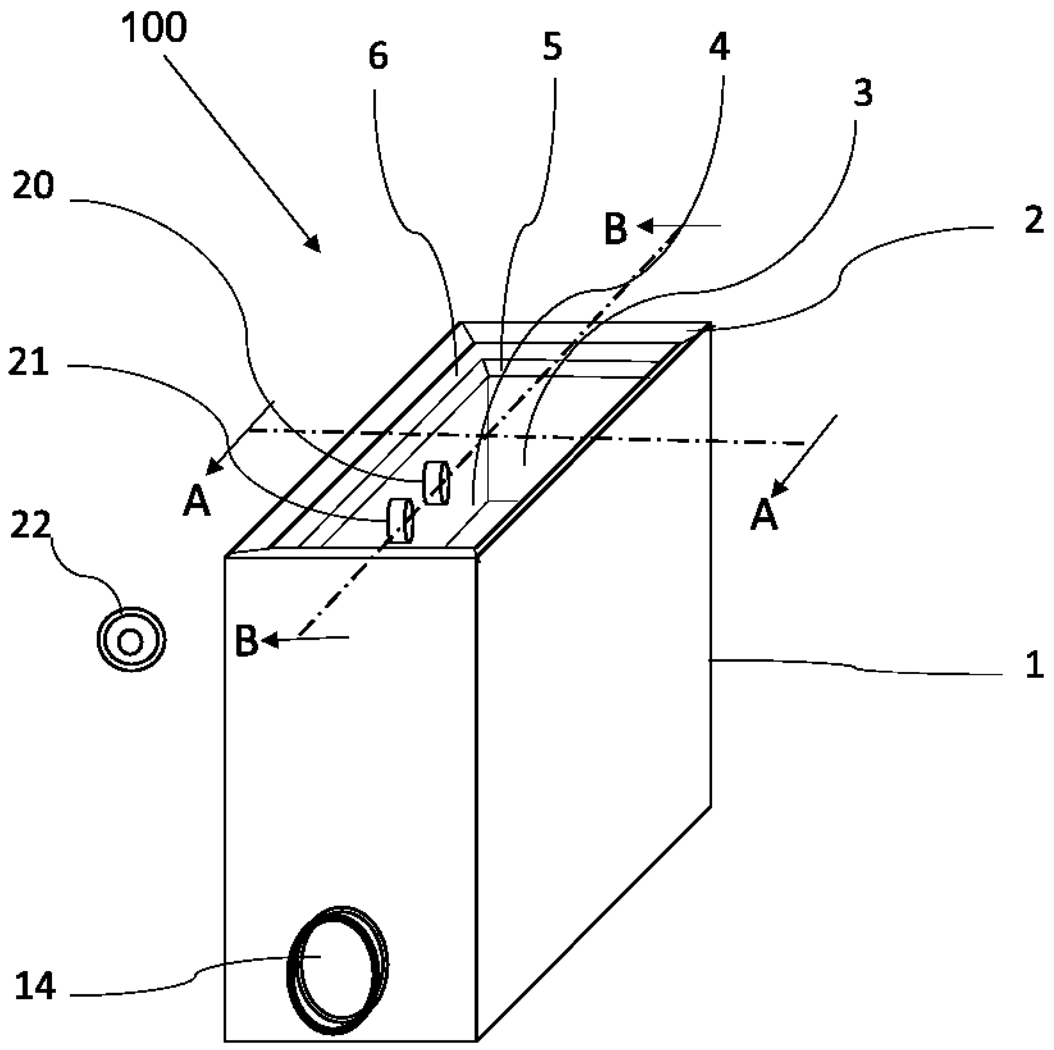
FIG. 1 is a perspective view of a disinfecting device of the present invention

For better understanding of the present invention and in order to exemplify how it may be implemented in practice, several embodiments are hereby described, which should be interpreted only as non-limiting examples, with reference to the accompanying figures. It is noted that the sizes and scale of the embodiments presented in the figures are exemplary and non-limiting.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein.

The term "disinfecting" as used herein means the process of eliminating or reducing harmful microorganisms. In particular the term "effectively disinfecting" means the process of eliminating or reducing harmful microorganisms within a brief exposure of a short time. The reduction of microorganisms may reach 99%, 99.9%, 99.99% or 99.999% of the initial amount of microorganisms on the disinfected organ.

The term "ozone" as used herein means a molecule of 3 oxygen atoms, with the chemical formula $O_3$. Ozone is formed from dioxygen by the action of corona discharge generator. It is reactive and unstable gas breaking down to dioxygen $O_2$.

The term "ambient air" as used herein means the device's external air environment, which is atmospheric air in its natural state, typically composed of 78% nitrogen, 21% oxygen, and the remaining 1% comprises of carbon dioxide, helium, methane, argon and hydrogen.

The term "other microorganisms" should be construed to include bacteria, including its spores, viruses, protozoa, mold and fungi.

The term "catalytic ozone filter" as used herein means high performance Honeycomb type ozone decomposing filter. Using a newly developed catalyst, activated carbon and a special honeycomb construction. The filter decomposes ozone back to oxygen.

Figure 2:
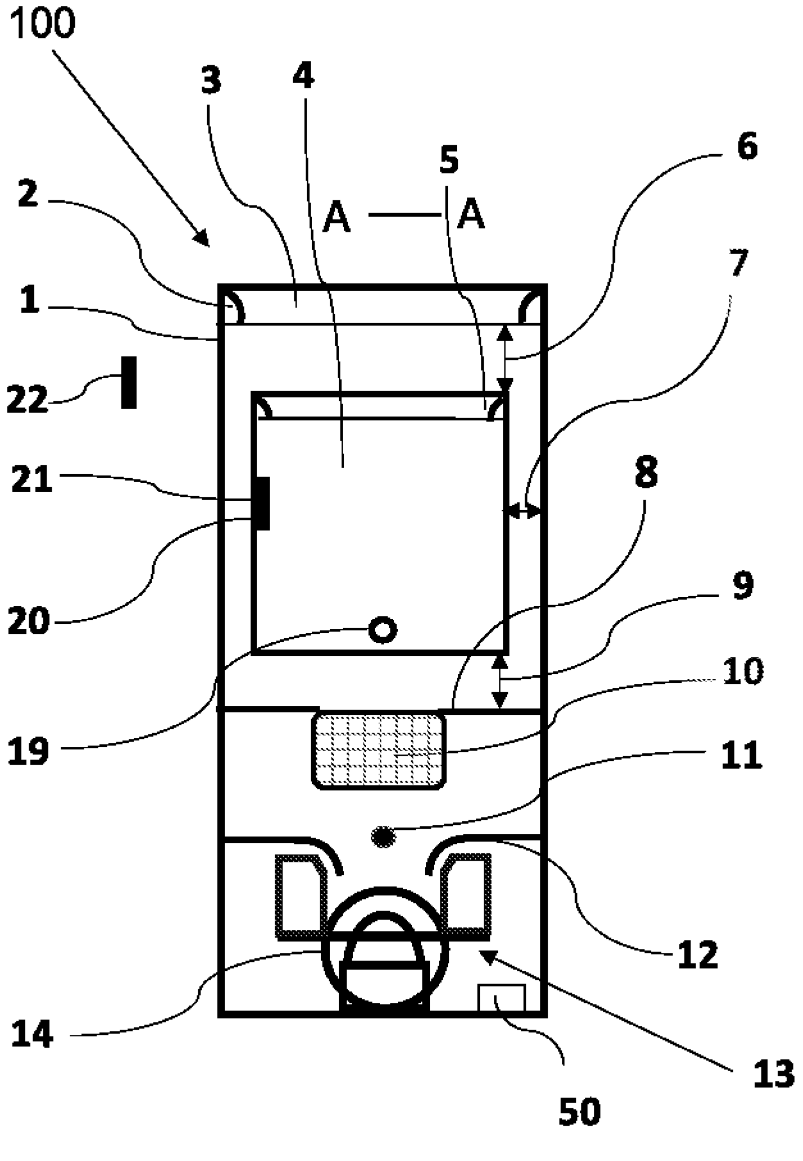
FIG. 2 is a cross-section A-A side view of the principal construction and the sensors of the disinfecting device presented in FIG. 1 according to an embodiment of the present invention.
Figure 3:
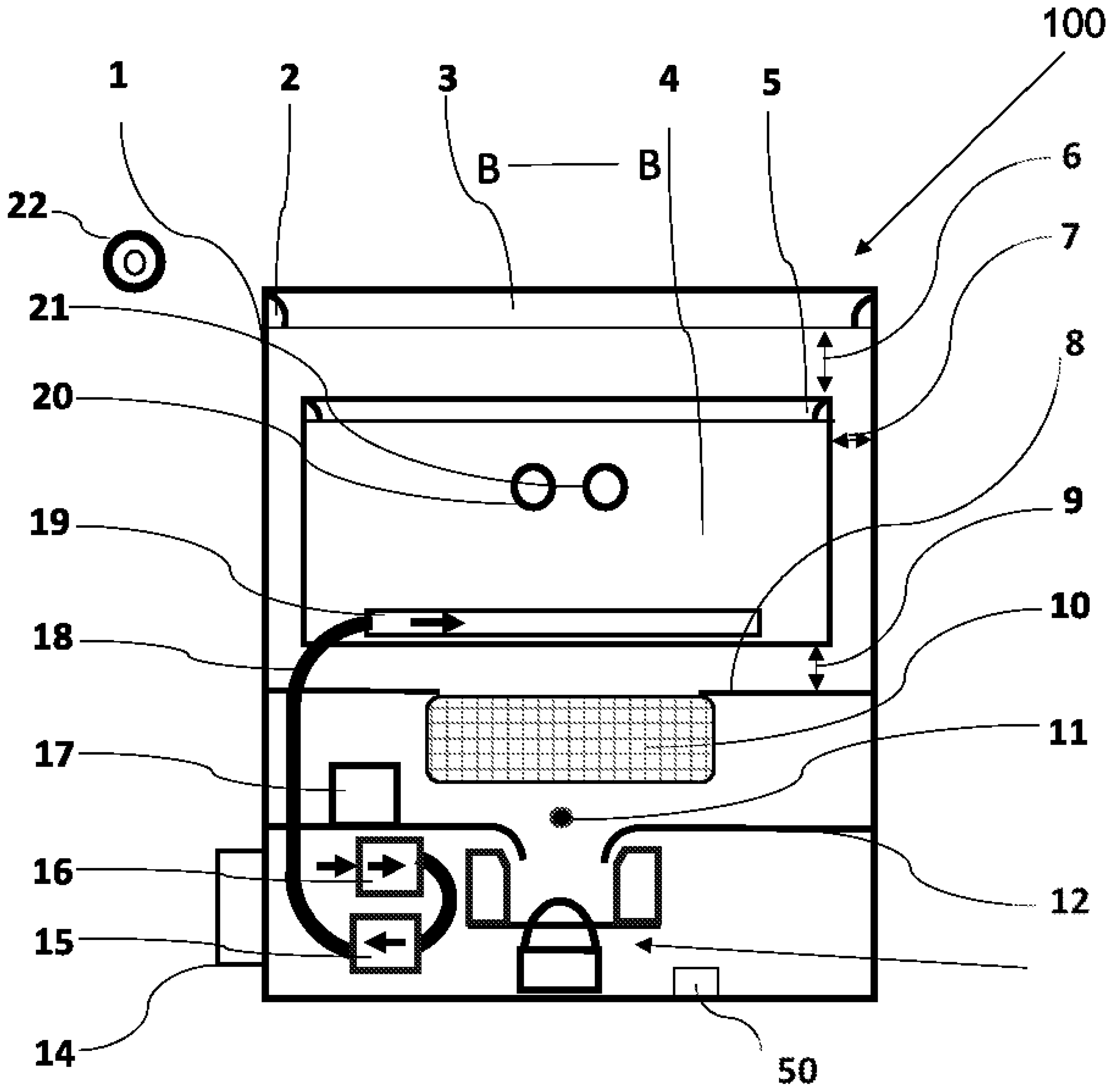
FIG. 3 is a cross-section B-B front view of the principal construction and the sensors of the disinfecting device presented in FIG. 1 according to an embodiment of the present invention.
Figure 4:
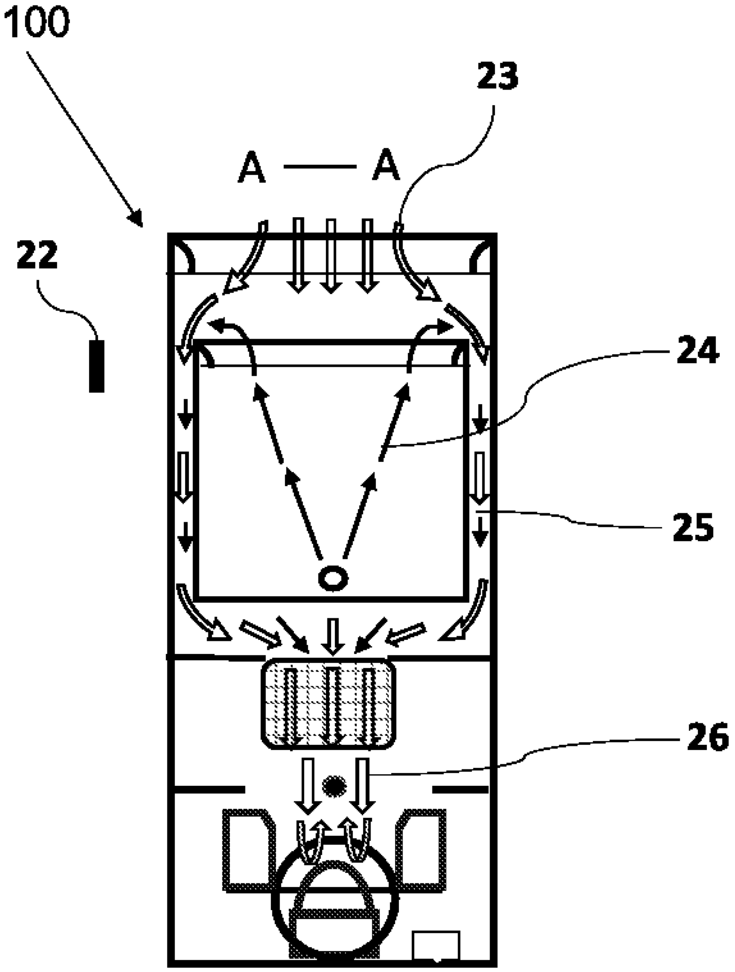
FIG. 4 is a cross-section A-A side view that describes the air and ozone flow of the disinfecting device presented in FIG. 1 according to an embodiment of the present invention.
Figure 5:
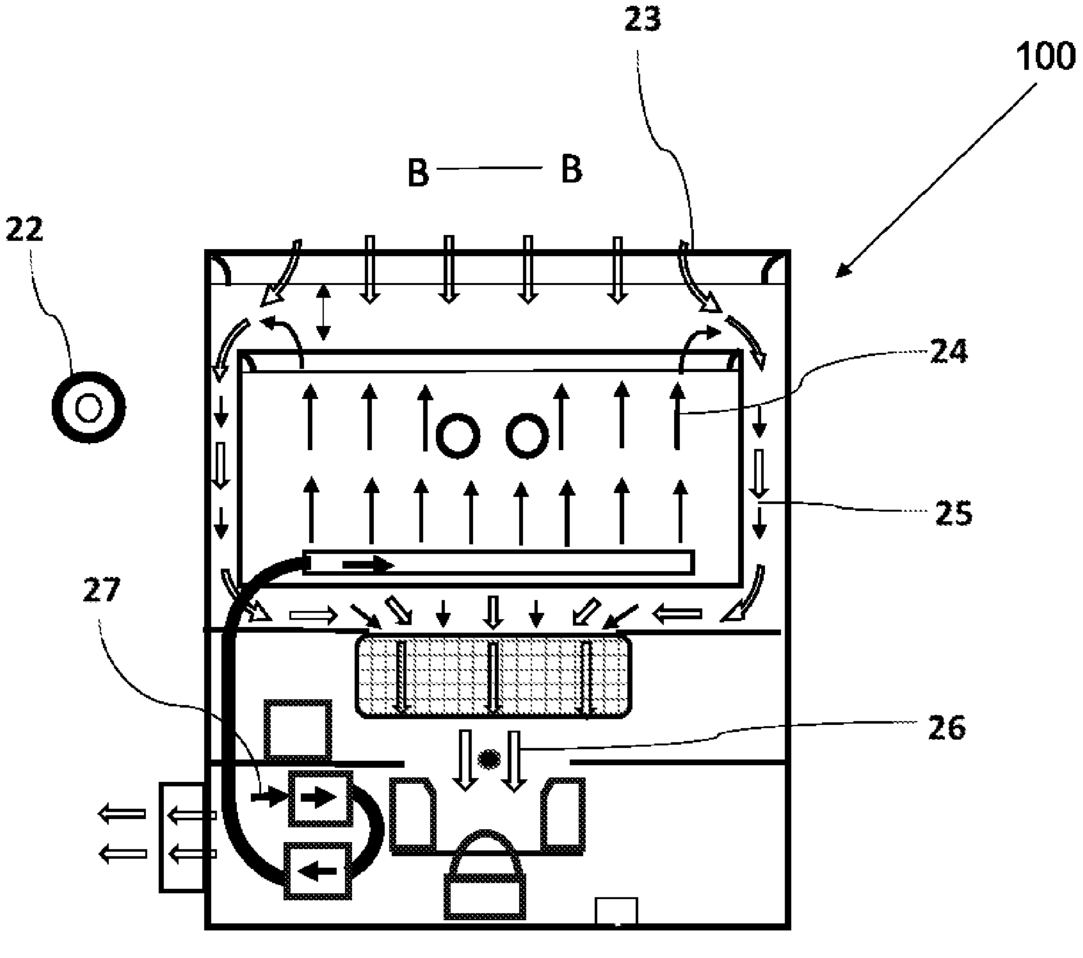
FIG. 5 is a cross-section B-B front view of that describes the air and ozone flow of the disinfecting device presented in FIG. 1 according to an embodiment of the present invention.
Figure 6:
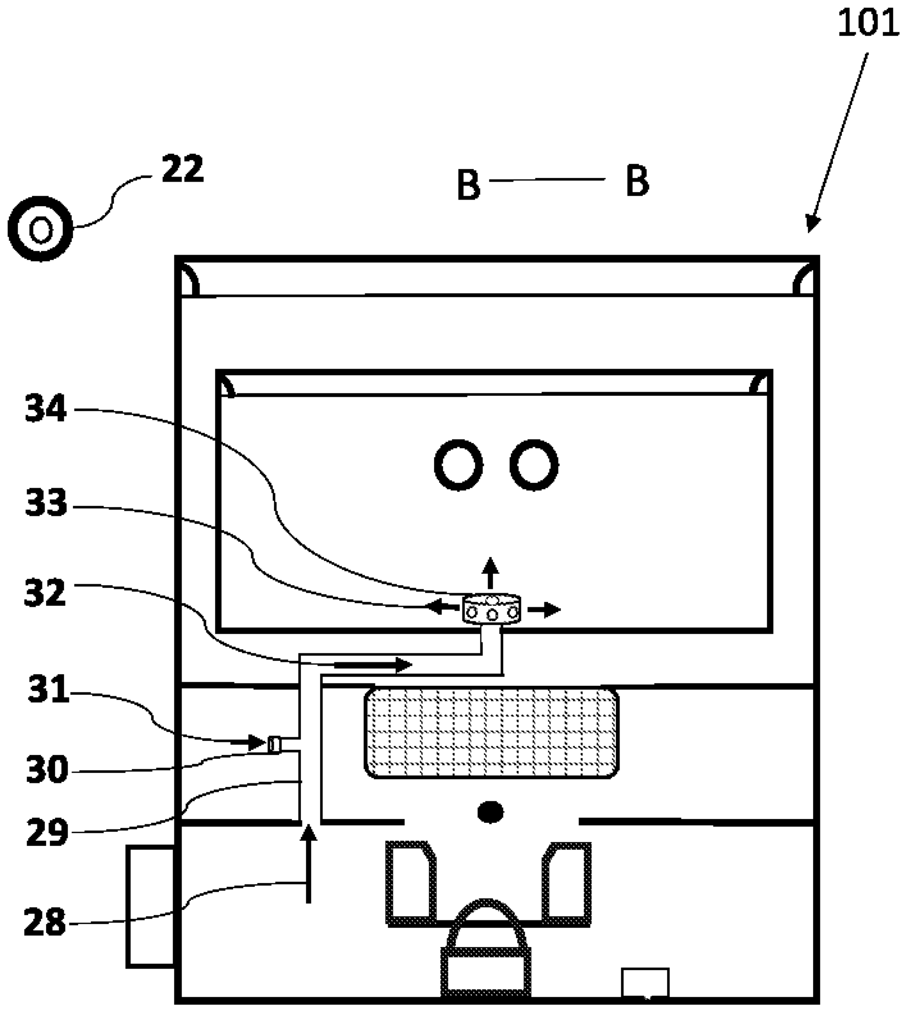
FIG. 6 is a cross section B-B side view that describes option A, of ozone distribution inside the disinfection chamber of the disinfecting device presented in FIG. 1 according to an embodiment of the present invention.
Figure 7:
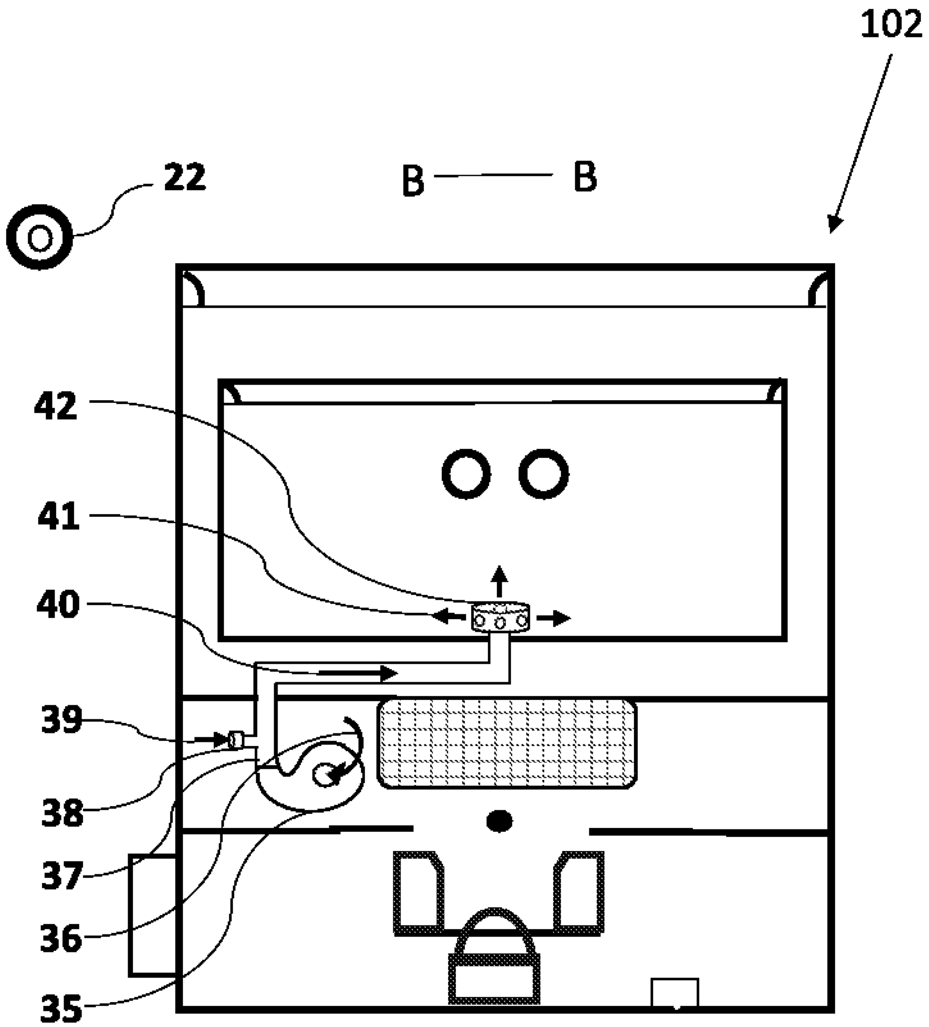
FIG. 7 is a cross section B-B side view that describes option B, of ozone distribution inside the disinfection chamber of the disinfecting device presented in FIG. 1 according to an embodiment of the present invention.
Figure 8:
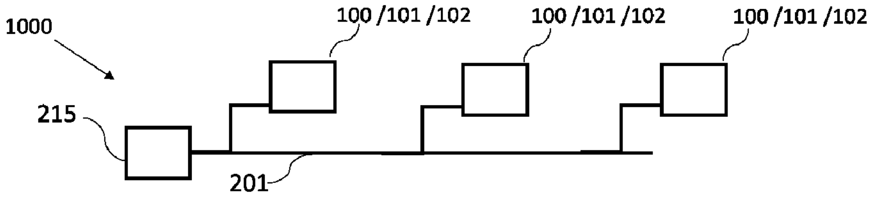
FIG. 8 is a schematic representation of a system of disinfection devices according to embodiments of the invention all connected to a central ozone generator according to an embodiment of the invention.
Figure 9:
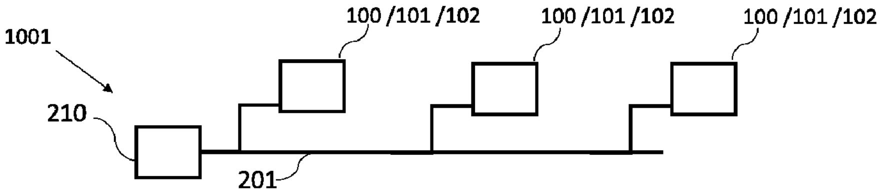
FIG. 9 is a schematic representation of a system of disinfection devices according to embodiments of the invention all connected to a central ozone filter according to an embodiment of the invention.
Figure 10:
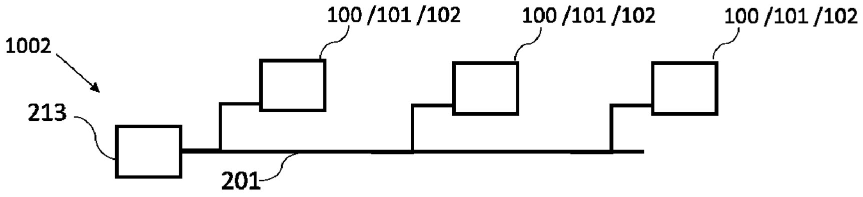
FIG. 10 is a schematic representation of a system of disinfection devices according to embodiments of the invention all connected to a central blower according to an embodiment of the invention.
Figure 11:
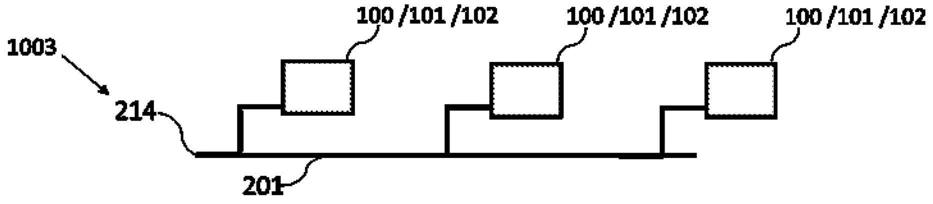
FIG. 11 is a schematic representation of a system of disinfection devices according to embodiments of the invention all connected to a central evacuation pipe according to an embodiment of the invention.

An exemplary embodiment of the invention will now be described referencing to the drawings:

FIG. 1, FIG. 2 and FIG. 3 describe the structure of a disinfection device according to one embodiment of the present invention. FIG. 4 and FIG. 5 describe the air and ozone flow in the device according to one embodiment of the present invention. FIG. 6 and FIG. 7 describe two different options of ozone distribution in the disinfection chamber of device according to one embodiment of the present invention.

All device parts and components may be constructed from materials resistant to ozone oxidation, such as stainless steel, PVC, ethylene propylene Rubber (EPDM), Teflon®, silicon and similar materials.

Housing 1 of disinfection device 100, can be a sealed construction (except for the top opening) having bottom and side walls designed to be free of air and ozone leakages. The top of the housing is open and used as hands insertion entrance for disinfection. In some embodiments only a portion of the top side of the housing is open. In some embodiments at least a portion of the top part of the housing is open to enable the insertion of the organ, e.g. hands, or disinfected element like masks or gloves. In some embodiments the opening is located at a top portion of one of the sidewalls of the housing. In some embodiments, the opening is partially on the top of the housing and partially on a sidewall of the housing. The dimensions of housing 1 are chosen for the intended use-they can be small for disinfecting accessories or large for disinfecting entire human body (without a head which is outside of the housing). The rest of the parts and components of the device are installed inside housing 1.

Entrance guide wall 2 is a profile which is attached to or extends from the four edges of housing 1. Its corners can be rounded to avoid air vortex or can have any other shape. Entrance guide wall 2 can be a separate part or part of the structure. In some embodiments, a UV lamp is installed at entrance guide wall 2 around the hands insertion area 3 in order to disinfect the entrance guide wall 2. In some embodiments, the UV lamp is turned on only in between users, i.e. it is turned off when hands are inserted into the chamber and turned on after they are removed before the next user inserts hands.

Hands insertion area 3 is the open area where the hands are inserted into the device. The area is permanently open to the environment. The dimensions of the hands insertion area 3 can be compatible with the size of the disinfected body. In FIGS. 1-5 the dimensions of the area is suitable for insertion of two hands for example a 15×40 cm rectangle, or can have any other dimension or shape.

Air entrance guide wall 2 can be installed on four edges of the hands insertion area 3.

In some embodiments, the top side of the housing 1 is attached to a lid (not shown) which may open automatically when a hand or pair of hands approaches the device 100. To this end, a motion (proximity) sensor is positioned in a suitable location to detect such motion and the sensor is in communication with an opening and evacuating mechanism which opens and closes the lid. In some embodiments, the housing 1 is placed with the hands insertion area 3 horizontally, the device can be positioned also such that the hands insertion area 3 is vertical and the hands are inserted into the device horizontally.

Chamber 4, is used as the disinfection chamber. It is a sealed chamber without air and ozone leakages, it can be connected in four places to housing 1 (the connection is not shown in the drawings). Its upper part is permanently open and used for hands insertion into the chamber. The chamber 4 is located under the hands insertion area 3 and inside housing 1 (at the center or off-center). The horizontal outer dimensions of the chamber 4 are smaller than the horizontal inner dimensions of housing 1 so that a gap defined by vertical duct 7 is created between all four edges of housing 1 and chamber 4. That gap is used as air ducts. The gap can be between 0.5 cm to 15 cm wide. In some embodiments, the gap is 0.5 cm, 1 cm, 2 cm, 5 cm, 10 cm or 15 cm wide. In some embodiments the gap is symmetric and even about the periphery of the chamber. In some embodiments the gap is unsymmetrical, wherein the chamber is off-center such that gap is not even in all sides around the chamber 4. In some embodiments, the bottom part of the housing is closed, and in some embodiments at least a portion of the bottom part of the housing is open to enable the air to be sucked and to maintain a low pressure in chamber 4.

The dimensions of chamber 4 can be small for disinfecting small accessories or large for disinfecting entire human body (without a head which is outside of the housing). The shape of chamber 4 can be a cube or any other shape for example a cone whose top is open.

Chamber guide 5, is a profile which is attached to the 4 edges of chamber 4. Its corners are rounded to avoid air vortex or can have any other shape. Chamber guide 5 is a separate part or part of the structure.

Suction duct 6, is a duct located under the hands insertion area 3, it is located between the entrance guide wall 2 and chamber guide wall 5. Suction duct 6 is used for suction of ambient air flow 23 and chamber flow 24 and is connected with suction duct 6, vertical duct 7, and horizontal duct 9 and through the filter 10 to the suction of the blower 13.

Vertical duct 7, can be located at four sides between housing 1 and chamber 4 and is used as a duct for the mixed air/ozone flow 25.

Filter partition 8, is ozone and air sealed plate connected to the inner walls of housing 1, and which partitions an upper portion from a lower portion of the housing 1. The upper portion may comprise the entrance guide wall 2, the hands insertion area 3, chamber 4, chamber guide 5, suction duct 6, vertical duct 7 and horizontal duct 9. The lower portion comprises the other components of the device 100 as detailed hereinbelow.

Horizontal duct 9, located below chamber 4 and above the filter partition 8 is used as a duct for the mixed air/ozone flow 25.

Ozone filter 10, is connected to filter partition 8 and may be a honeycomb catalyst and activated carbon filter, for ozone decomposition back to oxygen. The filter can reduce the low ozone concentration of the mixed air/ozone flow 25 (which is less than 15% from the ozone concentration inside chamber 4) to a concentration that is less than 0.05 PPMV that meets the FDA regulation. In some embodiments, the filter should be replaced periodically at the end of its life time to ensure that the device meets regulations. In some embodiments, the filter can contain a granular catalyst that regardless of the concentration of ozone entering it, at the exit from it there will be a constant ozone concentration and therefore there is no need to replace its granular catalyst. In some embodiments, two types of filters can be connected one after the other, for example a granular catalyst filter and thereafter a catalyst filter. In some embodiments, the ozone filter can be catalytic, carbon, 254 nm UV bulbs or other filter types. In some embodiment, the ozone filter can operate as a room air purifier, the room airflow that enters to the device is filtered by the device's filter.

Air velocity sensor 11, which may be located for example at the entrance to the blower 13, may send a signal to a control system which is in communication with the velocity sensor. The control system 50 may control the blower speed in response to the input received from the velocity sensor. The control system can stop the operation of the device when the air speed is below a predetermined value. For example when the air flow of the ambient air entering the device falls below a predetermined value, there will be ozone leakage from the opening and ambient pollution, velocity sensor 11 measures speed relative to the ambient flow and if the speed value falls below a predetermined value it stops the device.

Blower partition 12 is ozone and air sealed plate connected to the inner walls of housing 1. The air suction nozzle of blower 13 can be installed at partition 12.

Blower 13, of the embodiment depicted in FIGS. 1-5 is a centrifugal backwards curved blower, but other types can be used as well such as centrifugal forwards curved blower. The blower 13 moves the air in the device and creates suction in the volume above the blower partition 12 and high pressure in the space around it. Blower 13 sucks the ambient air into the device and discharges the air through the device air outlet 14. The RPM of the blower 13 can be controlled by the control system 50 according to the signal from the air velocity sensor 11.

Air outlet 14, may discharges the filter outlet air 26 from the device into the environment. A hose can be connected to the air outlet 14 in order to keep the air away from the device and discharge it to a location remotely from the device and far away from people, as an example 10 meter from air outlet 14. If the air is discharged to the environment, the device can also operate without a filter. in some embodiments the air outlet 14 can be connected to a central duct which evacuates the discharge air to a central duct which collects discharge airflows from a plurality of disinfection devices as part of a system comprising multiple disinfecting devices.

Ozone generator 15, as available in the art, generates gaseous ozone. Air from the outlet of air pump 16 enters the ozone generator 15 and by corona discharge effect, atmospheric oxygen can be converted to ozone. In order to extend the life and efficiency of the ozone generator 15, it can be cooled by the filter outlet flow 26. It can be installed inside the device or outside the device. The Ozone generator can be a ceramic plate ozone generator, UV lamp or other type of ozone generators which are available in the art.

An air pump 16, supplies air to the inlet of the ozone generator 15. The air inlet to pump 16 does not require mechanical filtration; ozone filter 10 filters the entrance air. The air fed to air pump 16 is from filter outlet flow 26 or ambient air or through an air dryer or through oxygen concentrator. The pump 16 can be installed inside the device or outside the device. A power supply 17, supplies through its controller adjustable high voltage to the ozone generator 15, hence maintaining a predetermined ozone concentration inside chamber 4. It can be installed inside the unit or outside the device.

An ozone supply tube 18, transfers the ozone from ozone generator 15 to chamber 4.

An ozone distributing tube 19, connected to the ozone supply hose 18, mounted at chamber 4 and may distribute the ozone evenly across chamber 4 through at least one hole or multiple holes dispersed along the tube. A blower can be mounted inside the disinfection chamber 4 and circulate the air to achieve a uniform ozone concentration inside chamber 4.

A motion sensor 20, can be placed at the chamber 4 and connected to the control system 50. The motion sensor is positioned for detecting when hands are inserted or removed from chamber 4. After the hands are inserted, a timer may activate the control system 50 and after a predetermined time, a light or voice signal informs the user that the disinfection is completed and the hands can be taken out. After the hands are removed, a signal device such as a light signal may inform the next user that the device is ready for hands disinfection. The operation of the ozone generator 15 can be stopped when there seems to be no need for disinfection, for example if motion sensor 20 does not feel insertion of hands for a long time, for example 1 minute, 2 minutes, 5 minutes, 10 minutes or more, the operation of the ozone generator 15 will be stopped until the hands are inserted again.

Ozone sensor 21, is located inside chamber 4 and is connected to the control system 50 either by wire or wirelessly (e.g. Bluetooth, or IR). It monitors and maintains a predetermined level of ozone concentration inside chamber 4, for example 10, 15, 20 or 30 PPMV.

Ozone external sensor 22, may be located outside the device were the outside ozone concentration is maximal, it is connected to the control system 50 either by wire or wirelessly (e.g. Bluetooth, or IR), if the ozone concentration is above a value of 0.07, 0.08, 0.09 or 0.10 PPMV (close to the maximum concentration allowed by OSHA regulation) an alarm can be operated or the device shuts off.

Ambient air flow 23, flows into the device through the hands insertion area 3 and enters into suction duct 6. The ambient air flow speed all over the hands insertion area 3 must be higher than a predetermined value (for example 0.2, 0.3 or 0.4 m/s) in order to prevent from ozone from exiting to the ambient. Speed sensor 11 measures a speed relative to ambient air flow 23 and "takes care" through the control system 50 that the speed does not fall below the predetermined value.

Chamber flow 24, is a small flow of air with the ozone concentration of chamber 4. It enters the suction duct 6 without any ozone escaping through the hands insertion area 3 to the environment. The amount of chamber flow 24 is equivalent to the very small amount pumped by the air pump 16 into the ozone generator 15 (for example 0.01 $m^3/h$). The strong flow and the vertical component of the ambient air flow 23 (for example 60 $m^3/h$) sweeps with it into suction duct 6 all the air with ozone that strives to leave chamber 4.

Mixed air/ozone flow 25 which flows in vertical duct 7, is a mixture of ambient air flow 23 and the very small amount of chamber flow 24. Mixed air/ozone flow 25 flows to horizontal duct 9 and from there to ozone filter 10

Filter outlet flow 26, is the filtered air flow at the outlet of ozone filter 10, it contains a negligible ozone concentration that meets the 0.05 PPM concentration required by the FDA standard. The filter can reduce the low ozone concentration of the mixed air/ozone flow 25 (which is less than 20% from the ozone concentration inside chamber 4).

Blower 13 sucks filter outlet flow 26 and discharges it through outlet 14 back to the environment.

Pump inlet air 27, is the air fed to pump 16. It can be from the filter outlet flow 26 or from ambient air. Pump inlet air 27 that enters pump 16 can also be supplied through an air dryer or through an oxygen concentrator. The pump inlet air 27 is supplied to the ozone generator were its oxygen is converted into gaseous ozone $O_3$.

The very small amount of ozone that the device emits into the environment decreased dramatically over time due to the instability and short half-life of ozone in fresh air, resulting in a quick decomposition back to oxygen.

Reference is now made to FIGS. 6 and 7 depicting another embodiment of the present invention, having a different ozone distribution mechanism than the one described in FIGS. 1-5. In all other respects, the components and of the embodiments depicted in FIGS. 6 and 7 can be identical to the components of the embodiment depicted in FIGS. 1-5. In the embodiments depicted in FIGS. 6 and 7, the ozone is distributed in the disinfection chamber through a distributor that is connected by a duct to a mixture of ozone from an ozone generator and air from an air blower or air inlet. Air inlet 28, is the air flow that enters supply duct 29 due to the pressure difference between the outlet pressure from blower 13 and the pressure inside chamber 4.

Supply duct 29, is the duct that connects the plenum where blower 13 is installed with distributor 34. Supply duct 29 passes through blower partition 12, filter partition 8 and the bottom of chamber 4, the passages through that parts are sealed against air leakages.

Ozone inlet tube 30, is a tube that penetrates into Supply duct 29 and is connected to the ozone outlet of ozone generator 15.

Ozone inlet flow 31, is the flow of air and ozone that flows from the outlet of the ozone generator 15 into ozone inlet tube 30, the aim of mixing both flows is to dilute the small amount of ozone coming out of generator 15, with the large amount of air inlet 28 so that the air and ozone that are discharged into chamber 4 will reach evenly all its volume.

Supply flow 32, is the mixture of air inlet 28 and ozone inlet 31, both flow through the supply duct 29 into the distributor 34.

Outlet flow 33 is the same flow as outlet flow 32, it exits from distributor 34 and distributes inside chamber 4 so that the ozone concentration all over chamber 4 is homogenous and without fluctuations of the concentration. The rate of outlet flow 33 is determined according to tests performed in order to determinate an even ozone concentration all over chamber 4.

Distributor 34, is connected to supply duct 29 and through holes or slots distributes outlet flow 33 evenly and without fluctuations of the concentration all over chamber 4. The holes or slots are distributed at the perimeter and at the top of distributor 34 and are located according to tests performed in order to determinate an even ozone concentration all over chamber 4.

FIG. 7 depicts another alternative mechanism for ozone dispersion. Ozone blower 35, mounted inside or outside of the device, sucks the air around it and discharges it into supply duct 37. The blower can be a constant speed or a variable speed.

Air inlet flow 36, is the air flow that enters ozone blower 35, it can be from any place downstream of filter 10 or from ambient air.

Supply duct 37, is the duct that connects ozone blower 35 with distributor 42. Supply duct 37 passes through blower partition 12, filter partition 8 and the bottom of chamber 4, the passages through those parts are sealed against air leakages.

Ozone inlet tube 38 is a tube that penetrates into supply duct 37 and is connected to the ozone outlet of the ozone generator 15.

Ozone inlet flow 39, is the air and ozone that flows from the outlet of the ozone generator 15 into ozone inlet tube 38, the aim of mixing both flows is to dilute the small amount of ozone coming out of generator 15, with the large amount of air inlet-B 36 so that the air and ozone that are discharged into chamber 4 will reach evenly all its volume.

Supply flow 40, is the mixture of air inlet 36 and ozone inlet-B 39, both flow through supply duct 37 into the distributor 42.

Outlet flow 41 is the same flow as supply flow 40, it exits from distributor 42 and distributes inside chamber 4 so that the ozone concentration all over chamber 4 is homogenous and without fluctuations of the concentration. The rate of outlet flow 41 is determined according to tests performed in order to determinate an even ozone concentration all over chamber 4.

Distributor 42, is connected to supply duct 37 and through holes or slots distributes the outlet flow 41 evenly and without fluctuations of the concentration all over chamber 4. The holes or slots are distributed at the perimeter and at the top of distributor 41 and are located accordingly to tests performed in order to determinate an even ozone concentration all over chamber 4.

Device Operation Method

There are many options to operate the device; one option is described here for demonstration purposes in a non-limiting manner.

The sensors and the components are connected to the device control system 50.

The inputs to the control system 50 are: the air velocity sensor 11, ozone sensor 21, external ozone sensor 22 and motion sensor 20.

The outputs of the control system 50 are: speed of blower 13, ozone production of the ozone system, the lights and display on the control panel, interface with other devices like opening a gate after the disinfection is performed correctly or print a certificate that disinfection was performed.

In one embodiment, the device is ready for hands disinfection after the following steps:

1. Blower 13 is activated. After reaching the target rpm of the blower 13, air velocity sensor 11 sends a signal to the control system 50 that the velocity of the ambient air flow 23 is above the predetermined air speed (blower 13 is working properly), for example, the air velocity of the ambient air flow 23 is above 0.3 m/s (the control system 50 can control the power provided to the blower so that the velocity is between 0.3 m/s and 0.4 m/s). The velocity that sensor 11 measures at its location is proportional to the velocity of ambient air flow 23.

2. Ozone generator 15 is activated. Ozone sensor 21 sends a signal to the control system 50 that the ozone concentration inside chamber 4 is above the predetermined concentration (ozone generator 15 is working properly), for example, the concentration is above 7 PPMV, (experiments found that disinfection of 99.9% from the virus SARS COV-2 requires a disinfection time of 15 seconds and an ozone concentration of at least 5.0 PPMV, the sensor is installed in chamber 4 where the concentration is lowest and the control system 50 controls so that the ozone concentration is between 7 PPMV and 9 PPMV).
3. External ozone sensor 22 sends a signal that the ozone concentration in the environment is below a predetermined value (no ozone hazard). According to OSHA's regulations, at the vicinity of a device that emits ozone to the ambient, the concentration of ozone must not rise to a value that is higher than 0.1 PPM. For example, ozone external sensor 22 can be placed outside the device next to the air discharge outlet 14 and the external ozone sensor 22 will stop the device if the concentration of ozone is for example higher than 0.08 PPM.
4. The user panel displays 'Device is ready for disinfection'.

The user inserts hands through the hands insertion area 3 and places them inside chamber 4. The motion sensor 20 senses movement and initiates a timer for a predetermined time (for example 15 seconds). After the predetermined time the user panel displaying 'Disinfection is completed' and the user removes the hands, the motion sensor 20 senses that hands were removed and the user panel display 'Device is ready for disinfection'. If the user removes the hands before the predetermined time, an alert will be given, for example a beep or an entry gate does not open. At higher ozone concentrations the disinfection duration can shorten to achieve a target level of disinfection (i.e. percentage of dead pathogen). The person of skill in the art would know how to make such adjustments.

The device can operate in other methods, such as turning the device off followed a certain time when it is not in use.

In a further aspect, with reference to FIGS. 8-11 the invention provides a system of disinfections devices. The system (1000, 1001 or 1002) may comprise at least one disinfection device or multiple disinfection devices according to the invention (e.g. 100, 101 or 102), with the modification that at least one of the blower, ozone generator and ozone filter are removed from the housing of the device, and replaced by central counterpart connected to the individual devices by a common duct 201. The system thus comprises at least one disinfection device and at least one central component selected from:

a. Central ozone generator 215 to provide ozone to a disinfection chamber of the at least one disinfection device.
b. Central ozone filter 210 to receive a mixture of ambient air and excessive ozone overflow from the at least one disinfection device and reduce the amount of ozone in an output air flow;
c. An evacuation pipe 211 for exhausting a mixture of ambient air and excess ozone from the at least one disinfection device.
d. A central blower 213 to motivate ambient air from a housing opening of the at least one disinfection device and excessive ozone overflow from a disinfection chamber through a suction duct of the disinfection device, through the central ozone filter and discharge said airflow to the environment.

The system further comprises a common conduct connecting the at least one central component to the at least one disinfection device. Each disinfection device in the system comprises:

a housing comprising an opening, an entrance guide wall, a disinfection chamber, a suction duct, and an air outlet;
the opening being located in the upper portion of the housing to allow insertion of an organ to be disinfected,
the entrance guide wall being attached to the circumference of the opening,
the disinfection chamber being located below the entrance guide wall and comprises a top opening and an ozone distributor being in fluid communication with the central ozone generator;
the suction duct comprises an entry located between the entrance guide wall and the disinfection chamber and extends toward the ozone treatment means;
in case the system lacks a blower the housing further comprises a blower that motivates ambient air from the housing opening and excessive ozone overflow from the disinfection chamber through the suction duct, through the ozone treatment means and discharge airflow from the device through the air outlet to the environment;
in case the system lacks a central ozone filter the housing further comprises an ozone filter in fluid communication with the suction duct and the air outlet;
in case the system lacks an ozone generator the housing further comprises an ozone generator to provide ozone to the disinfection chamber.

Such systems may be implemented in large facilities where a need for multiple disinfection devices are required, e.g. hospitals, schools, shopping malls, work places, convention centers, sport events stadiums and the like. End units of disinfection devices can be connected and share at least one mutual central element as detailed above (e.g. central ozone generator, central ozone filter, central evacuation pipe and central blower).

List of Embodiments

1. A disinfection device comprising:

a housing comprising an opening, an entrance guide wall, a disinfection chamber, a suction duct, an ozone generator to supply ozone to the disinfection chamber, a blower and an air outlet;
the opening is located in the upper portion of the housing to allow insertion of an organ to be disinfected,
the entrance guide wall is attached to the circumference of the opening or extends therefrom,
the disinfection chamber is located below the entrance guide wall and comprises a top opening and an ozone distributor being in fluid communication with an ozone generator;
the suction duct comprises an entry located between the entrance guide surface and the disinfection chamber and extends toward the ozone treatment means;
an ozone treatment means to receive a mixture of ambient air and excessive ozone overflow from the disinfection chamber and reduce the amount of ozone in an output air flow;
a blower that motivates ambient air from the housing opening and excessive ozone overflow from the disinfection chamber through the suction duct, through the ozone treatment means and discharge airflow from the device through the air outlet to the environment.

2. The device in embodiment 1, wherein the disinfection principle and method of hands disinfection is used for feet disinfection or full human body without head disinfection
3. The device of embodiment 1, wherein its disinfection principle and method of hands disinfection is applied for accessories such as masks, gloves, clothing, PPE, etc.
4. The device of embodiment 1, wherein the hands are inserted vertically or horizontally into the device.
5. The device of embodiment 1, wherein the air outlet can be connected to a hose to keep the air away from the user or to the surrounding air. If the air is discharged to the surrounding, the device can be operated without a filter.
6. The device of embodiment 1, comprising a control system for maintaining and changing the ozone concentration inside the chamber, air flow of the blower and other control options
7. The devices of embodiment 1 wherein a UV lamp is installed around the hands insertion area to disinfect the insertion area. The UV lamp can be turned on automatically or manually.
8. The device of embodiment 1, wherein the ozone filter can be catalytic filter, catalytic material, carbon filter, 254 nm UV bulbs or Granular Catalyst that regardless of the concentration of ozone entering it, at the exit from it there will be a constant ozone concentration and therefore there is no need to replace its granular In some embodiments two types filters can be connected one after the other, for example a Granular Catalyst filter and there after a catalyst filter.
9. The device of embodiment 1, wherein the Ozone generator is of a ceramic plate ozone generator, UV lamp or other type of ozone generators.
10. The device of embodiment 1 wherein the gas inlet to the ozone generator is air, oxygen from an Ozone concentrator or dry air from a passive absorption material or an active automatic air dryer with absorption material or other type of air dryer.
11. The device of embodiment 1 wherein a blower is mounted inside the disinfection chamber and circulates the air inside the disinfection chamber.
12. The device of embodiment 1, can be integrated with other devices or accessories as a system, for example, a door that opens only if disinfection has been performed, or a temperature measuring sensor that measures the hands temperature, etc.
13. The device of embodiment 1 that comprises a motion sensor that sends a signal to the control system when it feels that hands are inserted or removed from chamber.
14. The device of embodiment 1 that comprises an air velocity sensor that sends a signal to the control system for controlling the blower speed and to stop the operation of the device when the air speed is below a predetermined value.
15. The device of embodiment 1 that comprises an ozone concentration sensor inside the chamber.
16. The sensor sends a signal to the control system to maintain the predetermined the ozone concentration in the chamber or to stop the operation of the device when the ozone concentration is above a predetermined value.
17. The device of embodiment 1 which incorporates an ozone gas concentration sensor outside of the device which sends a signal to the control system to stop the operation of the device when the ozone concentration is above a predetermined value.
18. The device of embodiment 1, wherein the ozone is distributed inside the chamber through a tube with holes along its length.
19. The device of embodiment 1, wherein operates as a room air purifier, the room airflow that enters to the device is filtered by the device's ozone filter.
20. The device of embodiment 1, wherein its disinfection chamber and its air ducts are located in one place and all or some of its components are located in another place.

EXAMPLE

In order to test the feasibility of the innovation, prototypes of the device were constructed according to the invention and experiments were conducted. The experiments results are presented here as examples.

According to experimental results reported by Chun-Chieh Tseng et al. *Aerosol science and Technology,* 2006, 40, (9) 683-689, ozone levels of between 0.64 ppm and 5.20 ppm are required for inactivation of 90% to 99% depending on the type of virus tested and R/H level. Accordingly, stability experiments were conducted in a wide range of power (amps) provided to the ozone generator and a wide range of ambient air flow velocities over continuous operation of a prototype disinfection device 100 according to the invention as depicted in FIGS. 1-5 and detailed above. Each experiment was conducted over several hours, and was repeated few times. The operational conditions varied and were dependent on the time of the day, i.e. early morning with R/H ~55% and temperature of about 23° C., and afternoon with R/H ~75% and temperature 30° C. These experiments proved that the device creates stable ozone concentration across the disinfection chamber at 5 ppmv, 15 ppmv, 20 ppmv, 35 ppmv, 50 ppmv and up to 80 ppmv. When the velocity of the ambient air flow 23 is above 0.3 m/s, at any point of time during the experiment, the ozone concentration at the air outlet 14 and 1 cm above the hands insertion area 3 was 0 ppm.

The ozone concentration inside chamber 4 can be regulated with the ozone generation system to concentration between 4.0 PPMV and 30.0 PPMV.

The ozone concentration of the mixed air/ozone flow 25 (filter inlet) is less than 15% of the concentration inside chamber 4.

The ozone concentration at the Filter outlet flow 26 (discharge air outlet) is less than 0.05 PPMV.

Ozone outlet from the device (through hands insertion area 3) could not be detected, as its value is lower than the ozone value in the environment (assumed no ozone is leaking).

What is claimed is:

1. A disinfection device comprising:

a housing comprising an opening, an entrance guide wall, a disinfection chamber, a suction duct, an ozone generator to supply ozone to the disinfection chamber, a blower and an air outlet;

the opening is located in an upper portion of the housing to allow insertion of an organ to be disinfected, the entrance guide wall is attached to the circumference of the opening, the disinfection chamber is located below the entrance guide wall and comprises a top opening and an ozone distributor being in fluid communication with the ozone generator, and the suction duct comprises an entry located between the entrance guide wall and the disinfection chamber and extends toward an ozone filter.

2. The disinfection device of claim 1 wherein when the disinfection device is operating, the blower to motivate ambient air from a housing opening and excessive ozone overflow from the disinfection chamber through the suction duct, through the ozone filter and discharge airflow from the disinfection device through the air outlet to an environment.

3. The disinfection device of claim 2 wherein the ozone filter comprises a granular catalyst material.

4. The disinfection device of claim 1 wherein the ozone is distributed in the disinfection chamber through the ozone distributor that is connected by a duct to a mixture of ozone from the ozone generator and air from an air blower or air inlet.

5. The disinfection device of claim 1 wherein the suction duct extends towards a vertical duct located between the side walls of the housing and the sidewalls of the disinfection chamber.

6. The disinfection device of claim 1 wherein the ozone filter is in fluid communication with the suction duct and the air outlet, disposed upstream the air outlet, to receive a mixture of ambient air and excessive ozone overflow from the disinfection chamber and reduce the amount of ozone in an output air flow.

7. The disinfection device of claim 1 further comprising a control system being in communication with at least one sensor selected from an ozone level sensor located in the disinfection chamber, a motion sensor located near the top opening for detecting insertion of an organ to the disinfection chamber, an air velocity sensor located at the entrance to the blower and an ozone concentration sensor located outside the disinfection device.

* * * * *